(12) United States Patent
Choi et al.

(10) Patent No.: US 7,919,127 B2
(45) Date of Patent: Apr. 5, 2011

(54) *PULSATILLA* SPP. EXTRACTS EFFECTIVE IN BRAIN FUNCTION

(75) Inventors: Wonrack Choi, Seoul (KR); Chang-Kyun Han, Seoul (KR); Jung-Woo Seo, Seoul (KR); Guang-Jin Im, Ansan-si (KR); ChilMann Jung, Suwon-si (KR); Se Jun Yun, Seoul (KR); Wie-Jong Kwak, Seoul (KR); Tae Kon Kim, Suwon-si (KR); bongcheol Kim, Gwacheon-si (KR); Soomin Lee, Seoul (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 0 days.

(21) Appl. No.: 11/883,612

(22) PCT Filed: Feb. 3, 2005

(86) PCT No.: PCT/KR2005/000323
§ 371 (c)(1),
(2), (4) Date: May 2, 2008

(87) PCT Pub. No.: WO2006/083050
PCT Pub. Date: Aug. 10, 2006

(65) Prior Publication Data
US 2008/0248143 A1 Oct. 9, 2008

(51) Int. Cl.
*A61K 36/00* (2006.01)
(52) U.S. Cl. ........................................ 424/773
(58) Field of Classification Search .......... None
See application file for complete search history.

(56) References Cited

FOREIGN PATENT DOCUMENTS

| KR | 10-2000-0074182 A | 12/2000 |
|---|---|---|
| KR | 10-2002-0018695 A | 3/2002 |
| KR | 10-2005-0023711 A | 3/2005 |
| KR | 10-2005-0023712 A | 3/2005 |
| WO | WO 2004/069263 | 8/2004 |

OTHER PUBLICATIONS

*Pulsatilla* patens website (http://web.archive.org/web/20040826092936/http://montana.plant-life.org/species/pulsa_pate.htm—internet archived version from Aug. 2004).*
Ye (Phytochemistry (1996), vol. 42, pp. 799-802).*
Gao, Xiang-Dong et al.: "Pulsatilloside A and Anemoside $A_3$ Protect PC12 Cells from Apoptosis Induced by Sodium Cyanide and Glucose Deprivation", *Planta Med* 2003; 69; pp. 171-174.
Cheon, Seon Ah et al.: "The Anti-Inflammatory and Analgesic Actions of the Root of *Pulsatilla koreana*", *The Journal of Applied Pharmacology*, 8, pp. 207-212 (2000). Article Is in Korean however an English translation of the Abstract of the article appears on the first page.

* cited by examiner

*Primary Examiner* — Susan C Hoffman
(74) *Attorney, Agent, or Firm* — Frommer Lawrence & Haug LLP; Ronald R. Santucci

(57) ABSTRACT

This invention relates to Pulsatillae Radix extract for improving brain functions. More specifically, this invention relates to Pulsatillae Radix extract, its active fractions and a pharmaceutical product and a health food containing the same respectively having a protective activity against neurotoxicity and a growth inhibitory effect induced by beta-amyloid, an anti-oxidizing effect, a neuron proliferating effect and improving memory thereby effective in improving brain functions such as Mild Cognitive Impairment and dementia.

13 Claims, 4 Drawing Sheets

*PULSATILLA* SPP. EXTRACTS EFFECTIVE IN BRAIN FUNCTION

This application is a 371 of PCT/KR2005/000323 filed on Feb. 3, 2005, published on Aug. 10, 2006 under publication number WO 2006/083050 A1.

TECHNICAL FIELD OF THE INVENTION

The present invention relates to Pulsatillae Radix extract for improving brain functions. More specifically, this invention relates to Pulsatillae Radix extract, its active fractions, and a pharmaceutical product and a health food containing the same respectively having a protective activity against neurotoxicity induced by beta-amyloid, a growth inhibitory effect of beta-amyloid, an anti-oxidizing effect, a neuron proliferating effect and improving a weakened memory thus effective in improving brain functions such as Mild Cognitive Impairment (MCI) and dementia.

The growing percentage of a senile group in population has been a global trend including Korea and various kinds of degenerative senile diseases are led to great losses in society and economy. According to the statistics recently released by Alzheimer's Association in USA and American Aging Association, about 4 million Americans are suffering from dementia. In particular, dementia generally develops after the age of 60, rarely in their 50s. About 10.3% of Americans are suffering from dementia at present and about US $95 billion is being spent annually for therapeutic treatments of dementia patients. According to the report of Korea Institute for Health and Social Affairs, the percentage of dementia patients in Korean population was rapidly increased to account for 8.3% of senior citizens aged 65 or above in 1995 and it is expected to reach 9% by the year 2020, an increase of 0.7%. The above percentages, when applied to future estimate of Korean population according to Korea National Statistical Office, revealed that the dementia patients were 277,048 in 2000 (8.3% of the senior citizens aged 65 or above), 527,068 in 2015 (9% of the senior citizens aged 65 or above), and 619,132 in 2020 (9% of the senior citizens aged 65 or above), respectively. Dementia is an intractable disease that can devastate not only the patients themselves but also their direct family members and thus has been raised as a serious social and economic issue.

Mild cognitive impairment (MCI) refers to a health condition where cognitive functions such as memory, judgments, learning abilities are declined but are not too serious to meet the standards of dementia from the clinical point of view. However, the recent clinical studies have shown that it is very likely that the patients with MCI would develop a dementia. In clinical experiments, for example, it was shown that only 1-2% of normal a control group developed dementia each year while as much as 10-15% of MCI patients were developed into dementia. Therefore, it is important for MCI patients to get an early treatment in order to prevent the development of dementia. There are various reasons that may cause the development of dementia and Alzheimer disease has been known as one of the most feasible causes as such. The Alzheimer disease is characterized in that the protein beta-amyloid is deposited outside brain cells and learning ability and memory are drastically declined.

BACKGROUND OF THE INVENTION

Tacrine is the first FDA-approved drug developed in 1993 to treat Alzheimer disease. It is known to inhibit the secretion of acetylcholine produced in brains of Alzheimer disease patients at their early or intermediate stages thereby delaying the process of cognitive impairment. However, it was known to incur adverse effects in connection with liver and is hardly used at present. Aricept, another FDA-approved drug developed in 1996, acts by increasing the usage of acetylcholine and it can prolong its efficacy by a single dosage before bedtime. It has adverse effects such as nausea, diarrhea and fatigue but those symptoms are not so severe and are also easily disappeared. Nevertheless, both tacrine and aricept cannot reverse the onset of Alzheimer disease already developed and also it is not known how long the dementia patients should take the required drugs and how long the efficacy of administered drugs will remain effective. Therefore, there is a very urgent need to develop a therapeutic agent to treat dementia having excellent efficacies with little adverse effects.

Pulsatillae Radix is a perennial plant belonging to buttercup (Ranunculaceae) family of dicotyledon and has a few other names. The dried radix of *Pulsatilla chinensis* (Bge) Reg, *P. koreana* Nakai, *P. cernua* Var, *P. patens* and its species are used to prepare therapeutic agents having effects of defervescence, convergence, anti-inflammation, sterilization, etc., as well as an antidiarrheal resulted from dysentery. In Korean traditional folk medicinal therapies, it has been also used to treat malaria and neuralgia but there has been no scientific report that it has a therapeutic effect for treating dementia.

SUMMARY OF THE INVENTION

The inventors of the present invention have made intensive and thorough researches to develop a therapeutic agent for treating dementia by preventing neurotoxicity induced by beta-amyloid and an inhibitory effect on beta-amyloid formation, and also by having an anti-oxidizing effect, a neuron proliferating effect and improving a weakened memory. As a result, the inventors of the present invention finally succeeded in obtaining a useful extract and its active fractions from Pulsatillae Radix.

Therefore, an object of the present invention is to provide a useful extract and its active fractions from Pulsatillae Radix having a protective activity against neurotoxicity induced by beta-amyloid, an inhibitory effect on beta-amyloid formation, an anti-oxidizing effect, a neuron proliferating effect and improving a weakened memory.

Another object of the present invention is to provide a method for preparing the above useful extract and its active fractions from Pulsatillae Radix.

A further object of the present invention is to provide a pharmaceutical product and a health food containing the above useful extract and its active fractions obtained from Pulsatillae Radix effective in improving brain functions.

DETAILED DESCRIPTION OF THE EMBODIMENTS

This invention relates to Pulsatillae Radix extract, its active fractions, and a method for preparing the same.

Further, this invention also relates to a therapeutic agent comprising Pulsatillae Radix extract or its active fractions for improvement of brain functions, prevention and treatment of mild cognitive impairment, prevention and treatment of dementia, and a health food product comprising Pulsatillae Radix extract or its active fractions for improving brain functions.

This invention is described in greater details as set forth hereunder.

The present invention relates to Pulsatillae Radix extract for improving brain functions. More specifically, this invention relates to Pulsatillae Radix extract, its active fractions, and a pharmaceutical product and a health food containing the same, respectively having a protective activity against neurotoxicity induced by beta-amyloid, an inhibitory effect on beta-amyloid formation, an anti-oxidizing effect, a neuron proliferating effect and improving a weakened memory thus effective in improving brain functions such as Mild Cognitive Impairment (MCI) and dementia.

Examples of the Pulsatillae Radix to be used as starting material in the present invention are *Pulsatilla chinensis, Pulsatilla koreana* (synonym: *Pulsatilla cernua*), *Pulsatilla patens* and *Pulsatilla* sp., i.e., a plant belonging to buttercup (Ranunculaceae) family. The major uses of Pulsatillae Radix are anti-inflammation, convergence, hemostatic and antidiarrheal.

In a preferred embodiment of this invention, there is provided a method for effectively isolating Pulsatillae Radix extract and its active fractions having excellent therapeutic effects as set forth hereunder.

First, Pulsatillae Radix is minced and then extracted by using alcohol by adding about 5 to 10 times of a low grade alcohol with reference to the weight of the Pulsatillae Radix based on its herbal weight, preferably a $C_1$-$C_6$ alcohol, more preferably a MeOH or an EtOH solution. After performing the alcohol extraction 2-4 times the extract is filtered and then concentrated under reduced pressure to completely eliminate alcohol therein thereby facilitating easy solvent fractions to be followed. The extract is then completely dissolved or suspended in about 3 to 5 times (v/w) of distilled water with reference to the weight of the Pulsatillae Radix based on its herbal weight. Here, it is preferred to use a sufficient amount of water for complete dissolution of the extract but, due to the inconveniences in handling of a large amount of water, it is often proceeded further with the next steps even when the extract is not completely dissolved. Then, the resultant is added with an equal weight of a water-saturated low grade alcohol and then stirred at a rate of about 30 to 50 rpm for about 10 to 20 minutes and then allowed to generate separation of layers. The water-saturated low grade alcohol is filtered and then concentrated under reduced pressure to obtain an active fraction. The water-saturated low grade alcohol used above is a saturated solution of a low grade alcohol which is obtained by: adding distilled water to a low grade alcohol, stirring, allowing it to generate separated layers and collecting the water-saturated low grade alcohol. The above low grade alcohol is preferably a $C_1$-$C_6$ alcohol, more preferably a propanol or a butanol. The separation of layers is repeated 2-3 times. In obtaining a solvent fraction by using a low grade alcohol, if a little amount of the low grade alcohol is used the result of purification becomes poor thus lowering the yield of the extract and the amount of active ingredients. In contrast, if a large amount of the low grade alcohol is used it is not cost-effective. Therefore, it is preferable to use about 2 to 3 times (v/w) of a low grade alcohol with reference to the weight of the Pulsatillae Radix based on its herbal weight. The activities of thus prepared extract and its active fractions were tested and shown to be effective in protection activity against neurotoxicity due to beta-amyloid.

The column chromatography using Octadecyl silica resin (YMC*GEL ODS-A 12 nm, S-150 m) was performed to define the active fractions and compounds with the highest level of activities from the solvent fractions of the Pulsatillae Radix. The resin was used about 25 times of the weight of a sample. A step-gradient method was selected to use the solvent; that is, the amount of methanol in the solvent was increased gradually at the rate of 10% (v/v) starting from the initial 10% (v/v) methanol solution (to) about 2 to 3 times of the volume of the resin. The protection activity against neurotoxicity due to beta-amyloid was observed in the fractions with methanol solutions of 60% (v/v), 70% (v/v), and 80% (v/v), and of them; the highest effect as such was observed at 70% (v/v).

In animal experiments, where a control group not treated with scopolamine, a substance known to decline memory ability by inhibiting the transmission of a neurotransmitter, or any other drugs, was set at 100% and a group treated with scopolamine (1 mg/kg) was set at 0%, the administration of Pulsatillae Radix extract and its fractions in the above treated group 1 hour after the scopolamine treatment resulted in an improvement in memory ability. In addition, the active fraction which showed the highest activity in the above experiment had an inhibitory activity against the toxicities induced by hydrogen peroxide and Staurosporine, had a cell proliferation effect as well as alpha-secretase activity increasing effect. Further, the above group also showed an improved memory in an animal experiment conducted via Water Maze Test. Therefore, it is suggested that the Pulsatillae Radix extract (or its fractions) of the present invention will be useful for the treatment of MCI and dementia and it can be also formulated into a pharmaceutical product or a health food product.

In preparing the Pulsatillae Radix extract (or its fractions) of the present invention as a pharmaceutical product, it can be formulated into typical type of pharmaceutical preparations to be administered orally or parenterally in clinical studies. More specifically, it can be manufactured by using the typical additives such as a filler, a diluent, a binder, a wetting agent, a disintegrating agent, a surfactant and an excipient.

Solid preparations for oral administration are tablets, pins, powder, granules, capsules, etc. The above solid preparations are manufactured by adding at least one excipient such as starch, calcium carbonate, sucrose or lactose, gelatin to lignan, lactone compounds and their derivatives. In addition, lubricants such as magnesium stearate, and talc may be used in addition to the typical excipients.

Liquid preparations for oral administration are suspensions, solution, emulsions, syrups, and various excipients such as a wetting agent, a sweetener, an aromatic agent, a preservative may be used in addition to the typical diluents such as water and liquid paraffin.

Preparations for parenteral administration are a sterile water-soluble liquid, a water-insoluble solvent, suspensions, emulsions, a lyophilizing agent and suppositories. Examples of water-insoluble solvents and suspensions are vegetable oils such as propylene glycol, polyethylene glycol, olive oil and injectable esters such as ethylolate. Examples of the base for suppositories are witepsol, marcrogol, Tween 61, cacao butter, Sevum Laurinumn, glycerol gelatin and the like.

The content of active ingredients of the preparations in the present invention can be adjusted as appropriate according to the absorptivity, the rate of inactivation, rate of excretion of the active ingredients, age, sex and health conditions of a patient.

The Pulsatillae Radix extract (or its fractions) of the present invention is preferably administered in the range of about 10 to about 400 mg/kg, more preferably about 20 to about 200 mg/kg, and about 1 to 3 times daily.

Further, in another embodiment of the present invention, there is provided a health food product for therapeutic treatment of MCI and dementia and improvement of brain functions comprising the Pulsatillae Radix extract (or its fractions). The health food product of the present invention refers to a product manufactured by adding the Pulsatillae Radix extract (or its fractions) to general food products or by formulating it into capsules, powder, and suspensions, taking of which would result in a certain therapeutic effect in connection with health conditions but not causing any adverse effects even with long-term administration unlike conventional pharmaceutical drugs.

BRIEF DESCRIPTION OF THE DRAWINGS

The above and other objects and features of the present invention will become apparent from the following description of the invention, when taken in conjunction with the accompanying figures, wherein.

EXAMPLES

Figure 1:
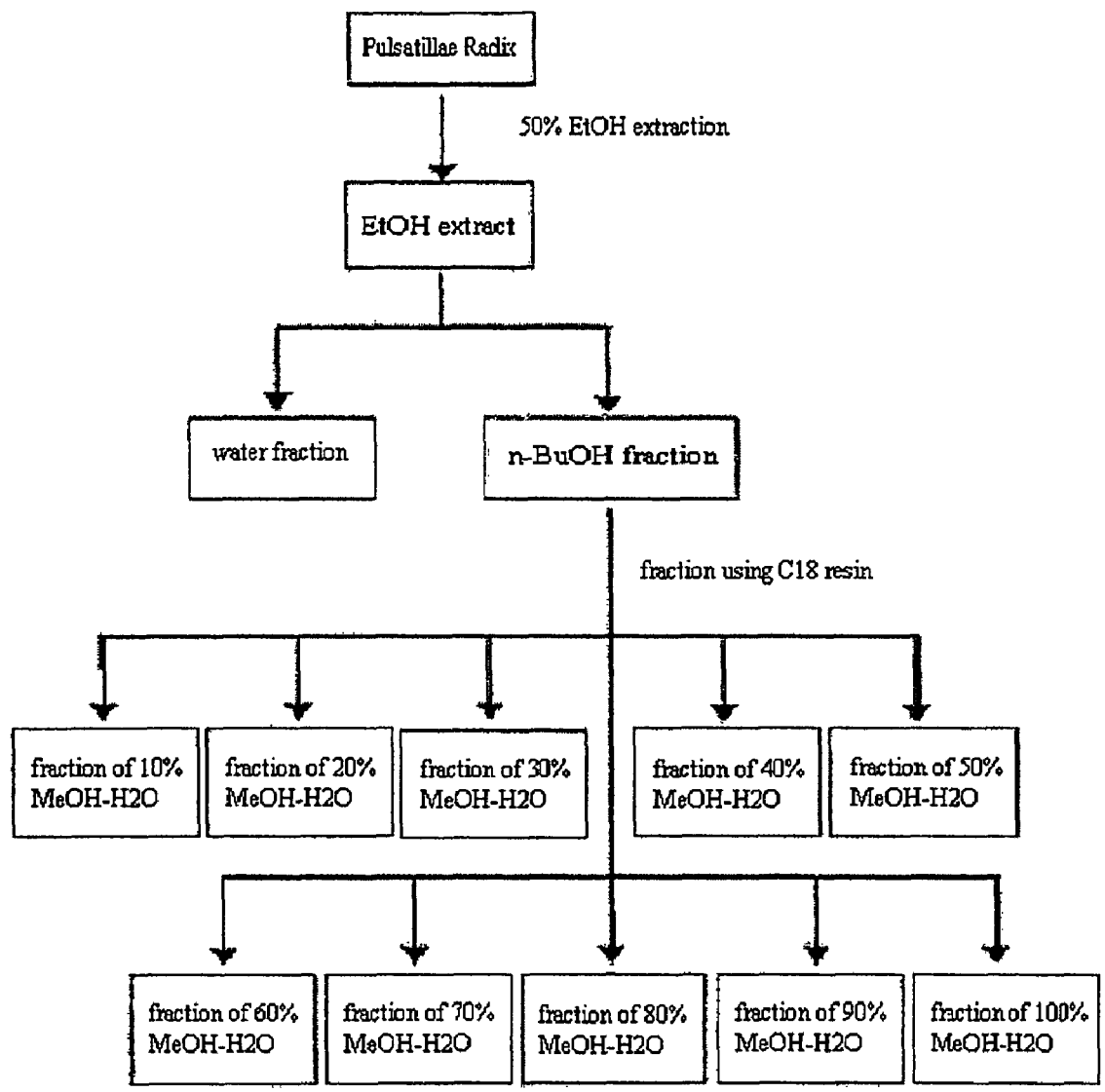
FIG. 1 shows a method of preparing Pulsatillae Radix extract and its fractions according to an embodiment shown in Example 2 of the present invention.

A better understanding of the present invention may be obtained in light of the following examples which are set forth to illustrate, but are not to be construed to limit the present invention.

Example 1

Extraction of Pulsatillae Radix and its Fractions

Two kilograms of minced dry Pulsatillae Radix underwent reflux extraction in 14 L of 50% ethanol for about 4 hours and the whole process was repeated once. The extract was filtered and then concentrated under reduced pressure at 50° C. using a rotary evaporator. The resulting concentrate was suspended in water so that the resulting volume becomes about 5 times (v/w) of that of the original herbal Pulsatillae Radix. Then, it was placed to a separation funnel after mixing with water-saturated n-butanol and then stirred for about 24 hours and allowed to generate separation of layers. The butanol layer on the top was collected, refractioned 2-3 times additionally, and the butanol layer and the remaining layer were concentrated using a rotary evaporator. Then the resultant was dried by removing the remaining solvent completely in the vacuum oven. Each of the resulting fractions was powdered and stored at −20° C. until it was used.

Example 2

Preparation of Subfractions of Pulsatillae Radix Fractions

The n-butanol fractions obtained in Example 1 were subjected to column chromatography using Octadecyl silica resin (YMC*GEL ODS-A 12 nm, S-150 m). The resin used was 500 g, about 25 times of the weight of a sample, and a step-gradient method was selected to use the solvent; that is, the amount of methanol in the solvent was increased gradually at the rate of 10% (v/v) starting from the initial 10% (v/v) methanol solution to about 2 to 3 times of the volume of the resin. As a result, a total of 10 fractions were obtained, which were concentrated using a rotary evaporator and dried in vacuum oven by removing all the remaining solvent. The above 10 fractions were stored at −20° C. until they were used.

Example 3

Method of Measuring the Inhibition Rate of Beta-Amyloid Induced Neurotoxicity

The Pulsatillae Radix extract and its n-butanol fractions obtained from Example. 1, and 10 fractions obtained from Example 2 were dissolved in 50% ethanol solution, diluted in MEM-α cell culture medium to a concentration of 20 μg/mL and 4 μg/mL, respectively, and then each cell was pretreated using 50 μL (it was confirmed that there was no vehicle effect on cells with EtOH final concentration of 0.5%). The cells used were SK-N-SH human neuroblastoma cell lines and they were divided into 96 wells on a plate with a concentration of $5 \times 10^3$, where each group was loaded into 3 wells, respectively. After 2 hours, cells were treated with beta-amyloid, which was dissolved in 100% DMSO, to a final concentration of 40 μM and then cultured in 5% $CO_2$ incubator at 37° C. for 48 hours. Upon completion of the above culture, the cells in each well were treated with 25 μL of MTT solution (5 mg/mL in PBS) and cultured again for 4 hours so that MTT could form formazan within the cells to measure viability of the cells. Then, the cell culture medium was removed and the cells were lysed with 100% DMSO and UV absorbance was measured at 550 nm via ELISA. The group not treated with beta-amyloid or any other drugs was assigned as control. The beta-amyloid induced cell toxicity was indicated in terms of beta-amyloid (%) based on the control group, the cell viability of which was set at 100%. The results of the cell viability (%) due to the above fractions are shown in the following Table 1, where each value respectively represents the mean value of these cells in 3 wells.

TABLE 1

| Classification | Conc. (μg/mL) | Inhibitory Rate (%) |
| --- | --- | --- |
| 50% EtOH extract | 20 | 78.4 |
| | 4 | 67.2 |
| n-BuOH fraction | 20 | 80.5 |
| | 4 | 67.7 |
| 10% MeOH fraction | 20 | 71.4 |
| | 4 | 66.7 |
| 20% MeOH fraction | 20 | 69.2 |
| | 4 | 67.4 |
| 30% MeOH fraction | 20 | 68.9 |
| | 4 | 67.8 |
| 40% MeOH fraction | 20 | 74.1 |
| | 4 | 68.1 |

TABLE 1-continued

| Classification | Conc. (μg/mL) | Inhibitory Rate (%) |
|---|---|---|
| 50% MeOH fraction | 20 | 71.2 |
| | 4 | 68.8 |
| 60% MeOH fraction | 20 | 79.2 |
| | 4 | 75.4 |
| 70% MeOH fraction | 20 | 83.6 |
| | 4 | 79.8 |
| 80% MeOH fraction | 20 | 81.1 |
| | 4 | 79.2 |
| 90% MeOH fraction | 20 | 11.6 |
| | 4 | 52.3 |
| 100% MeOH fraction | 20 | 51.6 |
| | 4 | 62.3 |
| Vehicle | 20 | 68.5 |

According to the above Table 1, the cell viability of SK-N-SH cell line at a concentration of 20 μg/mL treated with 50% ethanol extract and n-butanol fraction, respectively, was 78.4% and 80.5%, respectively, as compared to the normal cell viability of beta-amyloid induced cells of 68.5%, thus showing a significant level of difference. In case of cells treated with 60%, 70% and 80% methanol solution fraction all viabilities were also improved to 79.2%, 83.6% and 81.1%, respectively, thus showing that their high inhibitory effects to prevent the neurotoxicity induced by beta-amyloid. In Table 1, the highest inhibitory activity was observed in the cells treated with 70% methanol solution fraction where the inhibitory rate was 83.6% (20 μg/mL) and 79.8% (4 μg/mL), respectively, thus showing the cells have highest inhibitory activity against the beta-amyloid induced neurotoxicity.

Example 4

Measurement of the Inhibition Rate of Hydrogen Peroxide Induced Neurotoxicity

In order to study the inhibitory effect of 70% methanol solution fraction obtained in Example 2 on the toxicity induced by active oxygens, cells were treated with hydrogen peroxide to the concentration of 250 mM to induce cell toxicity and processed further as follows.

The cells were used HT22 neuroblastoma cell line and they were divided into a 96-well plate with a concentration of $5 \times 10^3$, where each group was loaded into 3 wells, respectively. The cells were divided into a control group and treated group and treated with active fractions to a concentration of 10 μg/mL and 100 μg/mL, respectively, cultured for 48 hours, treated with MTT solution (5 mg/mL in PBS) to be solubilized and OD (A570/A630) was measured. The group not treated with hydrogen peroxide or any other drugs were assigned as control. The hydrogen peroxide induced cell toxicity was indicated in terms of hydrogen peroxide (%) based on the control group, the cell viability of which was set at 100%. The results of the cell viability (%) due to the above fractions are shown in the following Table 2, where each value respectively represents the mean value of the cells in 3 wells.

TABLE 2

| | Inhibitory Rate (%) | | | |
|---|---|---|---|---|
| | | Hydrogen | 70% MeOH solution fraction | |
| Classification | Control | peroxide | 10 μg/mL | 100 μg/mL |
| 1st trial | 101.8 | 79.9 | 93.3 | 92.4 |
| 2nd trial | 99.4 | 77.1 | 77.4 | 83.5 |
| 3rd trial | 98.8 | 88.7 | 91.8 | 99.7 |
| Average | 100.0 | 81.9 | 87.5 | 91.9 |
| Standard Deviation | 1.3 | 4.9 | 7.1 | 6.6 |

From the Table 2, it was clearly shown that 70% methanol solution fraction reduced the cell toxicity induced by Hydrogen peroxide in HT22 cell line thus showing that the above fraction has an antioxidizing activity.

Example 5

Measurement of the Inhibition Rate Against Staurosporine-Induced Apoptosis

As the inhibitory effect of 70% methanol solution fraction on the active oxygen-induced toxicity was studied in Example 4, similar cell toxicity was studied by treating HT22 cells with staurosporine, which is known to affect the protein kinase C pathway, to a final concentration of 1 mM and the experiment was conducted as follows:

Cells were divided into a 96-well plate with a concentration of $5 \times 10^3$, where each group was loaded into 3 wells, respectively. The cells were divided into a control group and treated group and treated with active fractions to a concentration of 10 μg/mL and 100 μg/mL, respectively, cultured for 48 hours, treated with MTT solution (5 mg/mL in PBS) to be solubilized and then OD (A570/A630) was measured. The group not treated with staurosporine or any other drugs were assigned as control. The staurosporine induced cell toxicity was indicated in terms of staurosporine (%) based on the control group, the cell viability of which was set at 100%. The results of the cell viability (%) due to the above fractions are shown in the following Table 3.

TABLE 3

| | Inhibition Rate (%) | | | |
|---|---|---|---|---|
| | | | 70% MeOH solution fraction | |
| Classification | Control | Staurosporine | 10 μg/mL | 100 μg/mL |
| 1st trial | 101.8 | 71.3 | 71.6 | 78.4 |
| 2nd trial | 99.4 | 72.9 | 71.3 | 79.9 |
| 3rd trial | 98.8 | 71.6 | 72.6 | 78.4 |
| Average | 100.0 | 72 | 71.8 | 78.9 |
| Standard Deviation | 1.3 | 0.7 | 0.5 | 0.7 |

In the above Table 3, it is clearly shown that 70% methanol solution fraction reduces the cell toxicity induced by staurosporine in HT22 cell line thus showing that the above fraction has an antioxidizing activity.

Example 6

Effect of Cell Proliferation

As 70% methanol solution fraction was shown to have various effects on neurons, an experiment was performed to study whether its active fraction also has a neuron-proliferating activity as follows:

Cells of HT22 cell line were divided into a 96-well plate with a concentration of 5×10³, where each group was loaded into 3 wells, respectively. The cells were divided into a control group and treated group and treated with active fractions to a concentration of 10 μg/mL and 100 μg/mL, respectively, cultured for 48 hours, treated with MTT solution (5 mg/mL in PBS) to be solubilized and then OD (A570/A630) was measured. The group not treated with drugs were assigned as control, where the cell viability of a control group was set at 100%. The results of the cell viability (%) due to the above fractions are shown in the following Table 4.

TABLE 4

| | | Inhibition Rate (%) | |
|---|---|---|---|
| | | 70% MeOH solution fraction | |
| Classification | Control | 10 μg/mL | 100 μg/mL |
| 1$^{st}$ trial | 101.8 | 104.6 | 116.8 |
| 2$^{nd}$ trial | 99.4 | 101.2 | 111.3 |
| 3$^{rd}$ trial | 98.8 | 103.0 | 108.2 |
| Average | 100.0 | 102.9 | 112.1 |
| Standard Deviation | 1.3 | 1.4 | 3.5 |

From the Table 4, it is clearly shown that 70% methanol solution fraction has the cell-proliferating activity in HT22 cell line.

Example 7

Increase of α-Secretase Activity

Beta-amyloid, a major cause of dementia, is produced by processing of amyloid precursor protein (APP) by (-secretase. At normal conditions, APP is processed into sAPP (via (-secretase. Beta-amyloid induces toxicity that leads to apoptosis of neurons while sAPP-(has neurotrophic activities such as a neuron proliferating activity. Therefore, the activity of (-secretase is very important in prevention and treatment of dementia.

To study the effect of 70% methanol solution fraction obtained from Example 2 on the above-mentioned APP process, an experiment was conducted as follows using W4 cell line which produces APP in large amount.

The cells of W4 cell line were treated with 70% methanol solution fraction and then cultured for about 12 hours. The culture was then concentrated with TCA, western blotted and the resulting bands were quantitated by densitometry and the amount of sAPP (was measured. sAPP (is a product generated as a result of proteolysis of APP by (-secretase and the amount of sAPP (generated indirectly indicates the activity of (-secretase. The positive control in this experiment was a cell culture treated with Phorbol 12,13-dibutyrate (PDBu), an (-secretase activity inducing agent, to a final concentration of 1 mM which was used after concentration. The activity of (-secretase is calculated by comparing the amount of sAPP (in various groups with the amount of sAPP (in untreated cell culture.

TABLE 5

| | Relative Density | | | |
|---|---|---|---|---|
| | Negative | 70% Methanol solution fraction | | Positive Control |
| Classification | Control | 10 μg/mL | 100 μg/mL | (PDBu) |
| 1$^{st}$ trial | 62.9 | 129.6 | 148.4 | 226.5 |
| 2$^{nd}$ trial | 99.6 | 257.7 | 274.4 | 314.1 |
| 3$^{rd}$ trial | 137.5 | 239.2 | 161.8 | 327.2 |
| Average | 100.0 | 208.8 | 194.9 | 289.3 |
| Standard Deviation | 30.5 | 56.5 | 56.5 | 44.7 |

In the Table 5, it is clearly shown that 70% methanol solution fraction increases the activity of α-secretase in W4 cell line. The increase in the activity of α-secretase and the subsequent increase in the amount of sAPPα suggest that the production of beta-amyloid, the dementia-inducing material, is reduced.

Example 8

Passive Avoidance Test

According to the above result, Pulsatillae Radix extract and its active fractions suppress the cell toxicity induced by beta-amyloid in vitro and thus they are expected to alleviate the symptoms of Alzheimer's disease, a type of dementia known to be caused by neurotoxicity induced by beta-amyloid. To further identify the effect of the Pulsatillae Radix extract and its fractions in vivo on improving memory impairment, one of the major symptoms of dementia, Passive Avoidance test was performed using the Pulsatillae Radix extract and its fractions obtained in Examples 1 and 2 as follows.

The experimental device used was a shuttle box 50 cm (W)×15 cm (L)×40 cm (H). The shuttle box was divided into two rooms via a guillotine door, where one room was a light room provided with illumination while the other room was a dark room covered entirely with a black cloth thereby allowing the difference in illuminating effect.

First, a rat was placed in the light room and the guillotine door was opened while the light was being turned on. Then, the rat entered the dark room within 20 seconds to seek a dark place by instinct and as soon as the rat entered the dark room the guillotine door was closed. As described above, the time for the rat to transport from the light room to the dark room (hereinafter referred to as 'latency time') was measured and all rats participating in this experiment were trained through a training trial to enter the dark room within 20 seconds on the first day of experiment. The next day, the above trained rats were placed again into the light room with the light on and allowed to enter the dark room. Here, the rats were subject to an electric shock of 0.8 mA for 3 seconds via an electronic grid installed on the bottom of the room.

Twenty four hours after the above acquisition trial, the rats were again placed into the light room with the light on and allowed to enter the dark room. Here, the normal rats hesitated to enter the dark room by remembering the electric shock of the previous day. The latency time was measured by setting up the maximum latency time at 300 seconds.

In the above experiment, the effect of Pulsatillae Radix extract and its fractions on improving memory impairment was observed by measuring the level of improvement in memory for an experimental group treated with scopolamine (1 mg/mL), a drug known to reduce memory by inhibiting the transmission of a neurotransmitter, and then treated with Pulsatillae Radix extract 1 hour after the scopolamine treatment, where a control group not treated with scopolamine or any other drugs was set at 100%, and a group treated with scopolamine (1 mg/mL) was set at 0%.

Figure 2:
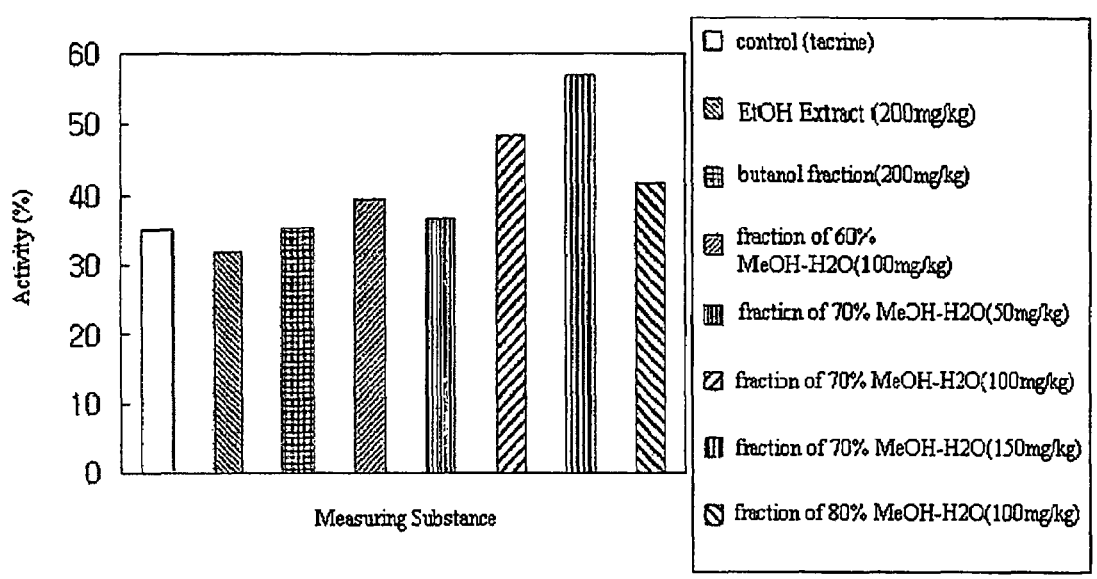
FIG. 2 is a graph showing the effectiveness of the Pulsatillae Radix extract and its fractions in improving scopolamine-induced memory deficits by a single oral administration of the Pulsatillae Radix extract and its fractions.

As a result, it was shown that Pulsatillae Radix extract and its fractions have the activity of preventing memory impairment resulted from scopolamine, which prevents the transmission of acetylcholine in the brain (FIG. 2).

When tacrine was orally administered as a control drug in the amount of 30 mg/L, it resulted in prevention of memory impairment by 35%. When Pulsatillae Radix extract obtained in Example 1 and its butanol fractions were orally administered in the amount of 200 mg/L, it resulted in activities of 31.9% and 35.2%, respectively. When 60%, 70% and 80% methanol solution fractions of Pulsatillae Radix extract obtained in Example 2 were orally administered in the amount of 100 mg/L, it resulted in activities with significance of 39.4%, 48.6% and 41.8, respectively. When 70% methanol solution fraction of Pulsatillae Radix extract obtained in Example 2 was orally administered in the amount of 150 mg/L, it resulted in activity with significance of 57.1%.

From the above results, it is apparent that Pulsatillae Radix extract and its fractions can improve declined memory observed as symptoms of dementia and MCI.

Example 9

Water Maze Test

Further to the above experiment confirming that Pulsatillae Radix extract and its fractions can improve declined memory, Water Maze Test was conducted to study the effect of Pulsatillae Radix extract and its fractions on improving learning ability and long-term memory impairment.

Experimental rats were anesthetized with sodium pentobarbital (50 mg/kg, i.p.) and then injected on both medial septa (AP: −0.2, L: ±0.3, H: −6.2) with 1 μg of $^{192}$saporin using stereotaxic technique. From the following day on, the rats were administered every day with 70% methanol solution fraction obtained in Example 2, which was prepared in 0.5% carboxymethyl cellulose (CMC), in the amount of 50, 100 and 200 mg/kg, respectively, to the experimental groups using a sterilized stainless steel injector for rats for a period of 3 weeks. The cylindrical water tank with 50 cm height used as a water maze in this experiment was filled with water at 22±2° C. to the height of 30 cm, and the necessary spatial equipments such as video camera, a laboratory table, a water-temperature controlling device on the laboratory table and the like were kept at regular locations. The escape platform was installed to a transparent circular acryl having a diameter of 12 cm and positioned 1.5 cm below the water level. The water maze was composed of 4 equal quadrants of northeast (NE), northwest (NW), southeast (SE) and southwest (SW). The platform was positioned at the center of the NE quadrant and one of the remaining quadrants was used as a starting place. In addition, the rats were trained 4 times daily for 7 days. Upon completion of the last training trial on the $7^{th}$ day, the rats were placed on a test trial for free swimming where the rats were allowed to freely swim for about 60 seconds with the platform removed. The behaviors of the experimental rats were videotaped. In the training trial, the time for the rats to reach the platform was measured while in the test trial for 60 seconds the time they stayed in the quadrant where the platform was positioned was measured.

Figure 3:
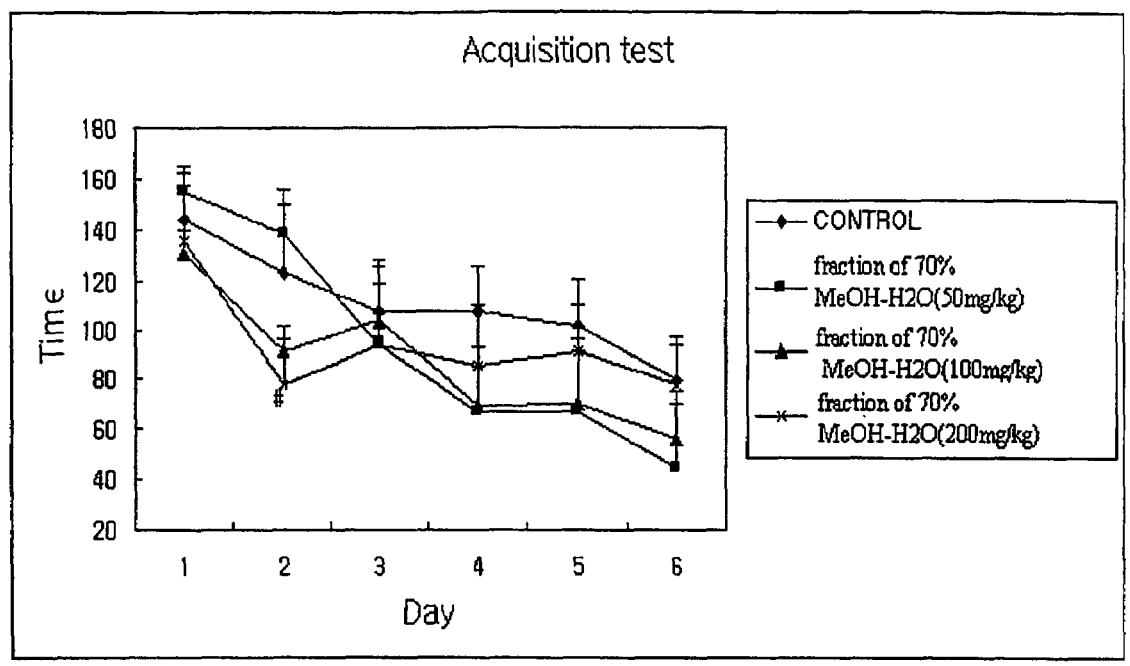
FIG. 3 is a graph showing the comparison results between a control group and groups treated with various concentrations of the active fractions of the Pulsatillae Radix extract regarding the effect of the active fractions of the Pulsatillae Radix extract via acquisition performance which measures the latency time required for experimental animals to reach escape platform within 180 seconds repeatedly conducted for a period of 6 days to evaluate the effect of water maze learning.

In the acquisition performance measuring the latency time to reach the platform within 180 seconds conducted for 6 days, on the $1^{st}$ day of the water maze learning, the latency time was 144.3±7.2 seconds for a control group, 154.9±9.4 seconds for a group treated with 7% methanol solution fraction (50 mg/kg) in Example 2, 130.8±21.7 seconds for a group treated with 70% methanol solution fraction (100 mg/kg) in Example 2, 135.8±11.9 seconds for a group treated with 70% methanol solution fraction (200 mg/kg) in Example 2, thus showing no significant difference among the groups. However, it was found by post-inspection, on the $2^{nd}$ day of the water maze learning, the latency time for the group treated with 70% methanol solution fraction (200 mg/kg) in Example 2 was 78.1±23.0 seconds thus showing a significant level of difference as compared to that of a control group (P<0.05) (FIG. 3).

Figure 4:
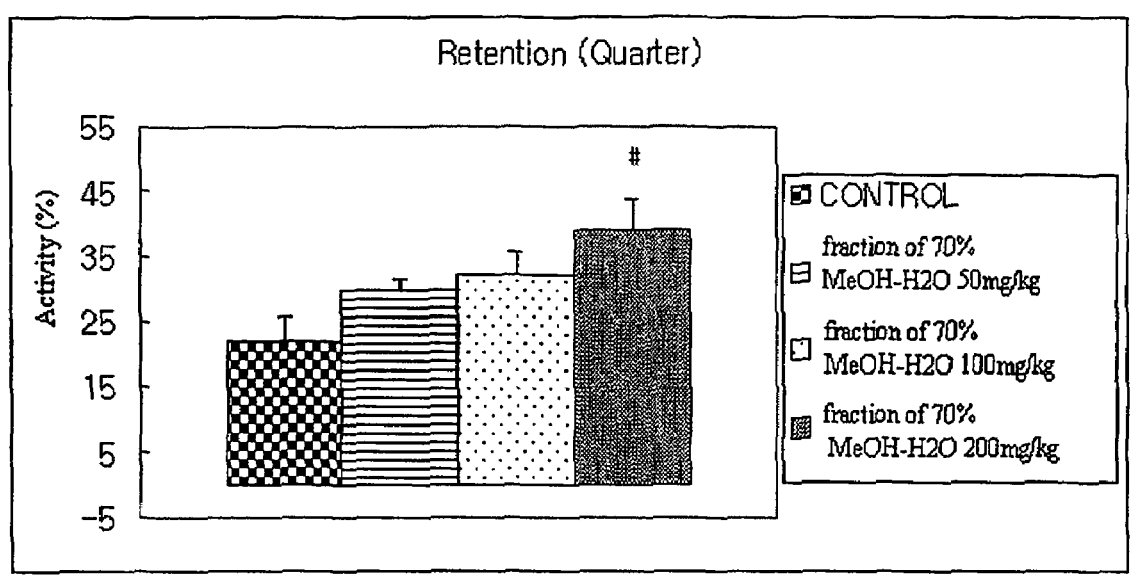
FIG. 4 is a graph showing the comparison results between a control group and groups treated with various concentrations of the active fractions of the Pulsatillae Radix extract regarding the effect of the active fractions of the Pulsatillae Radix extract via defective performance which measures the latency time required for experimental animals to stay the quadrant where the escape platform was placed on the 7th day, the final day of the water maze learning, after removing the escape platform to evaluate the effect of water maze learning.

Further, in the defective performance performed on the $7^{th}$ day where the retention time was measured on the quadrant where the platform was located after removal of the platform, there was a significant level of difference observed among the groups: that is, the retention time was 21.8±1.8% for a control group, 29.6±3.4% for a group treated with 70% methanol solution fraction (50 mg/kg) in Example 2, 32.1±4.7% for a group treated with 70% methanol solution fraction (100 mg/kg) in Example 2, 38.8±7.6% for a group treated with 70% methanol solution fraction (200 mg/kg) in Example 2 (P<0.05) (FIG. 4). Therefore, it is apparent that active fractions of Pulsatillae Radix extract can improve spatial learning and memory ability.

As stated above, it is clear that active fractions of Pulsatillae Radix extract have effects to improve declined memory ability and learning ability which are observed as major symptoms in dementia and MCI.

Example 10

Toxicity Test

To study the toxicity of a single oral administration of active fractions of Pulsatillae Radix extract 5 each sex of Sprague-Dawley (SD) rats were respectively administered with a test material in the amount of 2,000 mg/kg, 1,000 mg/kg, while a control group was administered with an excipient. The rats were then observed for two weeks with respect to mortality, general symptoms, change in body weight, and autopsy findings. The result showed that all rats survived and also there were no abnormal symptoms observed from the rats in connection with the administration of the test material. In addition, there were no abnormal symptoms observed in body weight and autopsy findings in connection with the administration of the test material. From the above results showing that no mortality or abnormal symptoms, change in body weight, and autopsy findings were observed by the administration of the test material, it was concluded that the minimal lethal dosage exceeds 2,000 mg/kg in both male and female SD rats. Further, an experiment was conducted on the groups of SD rats by orally administering a single dose of active fractions of Pulsatillae Radix extract in the amount of 2,000 mg/kg, 1,000 mg/kg, 500 mg/kg, and 100 mg/kg of, respectively, to each group, and the result showed that no mortality or abnormal symptoms, change in body weight, and autopsy findings were observed by the administration of the test material.

Preparation Example 1

Manufacture of Powder and Capsules

One hundred milligrams of Pulsatillae Radix extract (or its active fractions) was mixed with 14.8 mg of lactose, 3 mg of crystalline cellulose, and 0.2 mg of magnesium stearate. The mixture was filled into No. 5 gelatin capsules using an appropriate device.

Preparation Example 2

Manufacture of Injections

Fifty milligrams of Pulsatillae Radix extract (or its active fractions) was mixed with 180 mg of mannitol, 26 mg of $Na_2HPO_4.12H_2O$, and 2,974 mg of distilled water. The mixture was filled into a bottle and sterilized by heating at 20° C. for 30 minutes.

Preparation Example 3

Manufacture of Health Foods

Health foods were manufactured based on a daily administration basis by mixing 0.3 mg of Pulsatillae Radix extract (or its active fractions) with powdered vitamin E, ferrous lactate, oxidized zinc, nicotinic acid amide, vitamin A, vitamin B1 and B2.

The composition of the above health foods is as follows (daily dosage per person):

| | |
|---|---|
| Active ingredient | 300 mg |
| Ginseng extract | 100 mg |
| Green tea extract | 100 mg |
| Vitamin C | 100 mg |
| Powdered Vitamin E | 120 mg |
| Ferrous lactate | 2 mg |
| Oxidized zinc | 2 mg |
| Nicotinic acid amide | 20 mg |
| Vitamin A | 5 mg |
| Vitamin B1 | 2 mg |
| Vitamin B2 | 2 mg |
| Corn starch | 200 mg |
| Magnesium stearate | 20 mg |

As stated above, the Pulsatillae Radix extract and its active fractions can prevent the beta-amyloid induced neurotoxicity, and have the effects of inhibiting the generation of beta-amyloid, anti-oxidation activity, proliferation of neurons, improving learning and memory abilities, are thus expected to be useful for treating mild cognitive impairment (MCI) and dementia and they can be used to manufacture pharmaceutical drugs for improving brain functions as well as health foods.

The invention has been described in detail with reference to preferred embodiments thereof. However, it will be appreciated that those skilled in the art, upon consideration of the disclosure, may make modifications and improvements within the scope and spirit of the invention.

What is claimed is:

1. A method of treating dementia or mild cognitive impairment which comprises administering to a patient in need thereof, a therapeutically effective amount of a pharmaceutical composition comprising Pulsatillae radix extract wherein said Pulsatillae radix comprises *Pulsatilla patens* or *Pulsatilla koreana*.

2. The method of claim 1, wherein the Pulsatillae Radix extract contains an active fraction for treating dementia or mild cognitive impairment obtained by the steps comprising:
   (a) extracting Pulsatillae radix by using a $C_1$-$C_6$ alcohol to obtain an alcohol extract;
   (b) concentrating said alcohol extract under reduced pressure followed by layer separation using a water-saturated $C_1$-$C_6$ alcohol to obtain an alcohol fraction; and
   (c) obtaining an active fraction from said alcohol fraction by purifying via column chromatography.

3. The method of claim 2, wherein the $C_1$-$C_6$ alcohol in step (a) is 50% ethanol.

4. The method of claim 3, wherein the $C_1$-$C_6$ alcohol in step (b) is n-butanol.

5. The method of claim 4, wherein the elution solvent used in purifying via column chromatography is a 60 to 80% methanol solution.

6. The method of claim 5, wherein the treating dementia or mild cognitive impairment is a lowering of beta-amyloid induced neurotoxicity.

7. The method of claim 5, wherein the treating dementia or mild cognitive impairment is a lowering neurotoxicity induced by active oxygens.

8. The method of claim 5, wherein the treating dementia or mild cognitive impairment is an increase of neuron proliferating activity.

9. The method of claim 5, wherein the treating dementia or mild cognitive impairment is an increase of alpha-secretase activity.

10. The method of claim 5, wherein the elution solvent used in purifying via column chromatography is a 70% methanol solution.

11. The method of claim 1, wherein said Pulsatilla radix is *Pulsatilla koreana*.

12. The method of claim 2, wherein the method is for treating dementia.

13. The method of claim 2, wherein the method is for treating mild cognitive impairment.

* * * * *